United States Patent [19]

Golubkov et al.

[11] 4,357,941

[45] Nov. 9, 1982

[54] INSTRUMENT FOR MARKING OUT THE CENTRAL OPTICAL ZONE OF THE CORNEA

[76] Inventors: Boris P. Golubkov, ulitsa Chkalova, 9/19, kv. 19, Khimki Moskovskoi oblasti; Svyatoslav N. Fedorov, ulitsa Valtera Ulbrikhta, 2a, kv. 40, Moscow, both of U.S.S.R.; Valery V. Durnev, deceased, late of Moscow, U.S.S.R.; by Tamara S. Durneva, administratrix, ulitsa Lavochkina, 44, korpus 2, kv. 442, Moscow, U.S.S.R.

[21] Appl. No.: 191,707

[22] Filed: Sep. 29, 1980

[51] Int. Cl.³ .............................................. A61D 1/00
[52] U.S. Cl. ................................. 128/316; 128/305.1
[58] Field of Search .................... 128/305, 305.1, 310, 128/316, 303 R

[56] References Cited

U.S. PATENT DOCUMENTS 2,473,968  6/1949  Paton .................................. 128/305
3,990,453  11/1976  Douvas et al. ..................... 128/305

FOREIGN PATENT DOCUMENTS 2362157  11/1974  Fed. Rep. of Germany ...... 128/305
2365891  9/1976  Fed. Rep. of Germany ... 128/305.1
2811869  9/1979  Fed. Rep. of Germany ... 128/305.1
158650  3/1960  U.S.S.R. ............................ 128/310

Primary Examiner—Kyle L. Howell
Assistant Examiner—Daniel P. Burke
Attorney, Agent, or Firm—McAulay, Fields, Fisher, Goldstein & Nissen

[57] ABSTRACT

An instrument for making out the central optical zone of the cornea having an oblong body featuring the edge of one of its ends sharpened, while the diameter of the body across said end equals a preset diameter of the central optical zone, and a sight is accommodated inside the body square with the longitudinal axis thereof, the sighting point of said sight lying on the longitudinal axis of the oblong body of the instrument.

15 Claims, 3 Drawing Figures

INSTRUMENT FOR MARKING OUT THE CENTRAL OPTICAL ZONE OF THE CORNEA

BACKGROUND OF THE INVENTION

The present invention relates to ophthalmological equipment and is concerned more specifically with an instrument for marking out the central optical zone of the cornea primarily for surgical correction of myopia of different degrees.

Surgical methods of correction of myopia have found widespread application within the past few years, wherein a number of incisions are made in the cornea causing the change of the curvature thereof. One of the most important requirements of the method is to precisely locate the place where the incisions are to be made, inasmuch as even a negligible deviation from an accurate location will badly affect the result of the operation or even bring to nought the effect of the operation at all. Of special importance is not to affect the central optical zone of the cornea whose size is individual for every patient. That is why even an experienced continuously practising surgeon can err in locating the position of the optical zone of the cornea. Unfortunately the position of the optical zone has so far been located by visual estimation.

OBJECTS AND SUMMARY OF THE INVENTION

It is therefore a primary and essential object of the present invention to provide a special instrument for marking out the central optical zone of the cornea.

It is another object of the present invention to attain a higher quality and accuracy of surgical correction of myopia.

It is a further object of the present invention to attain a higher rate of such an operation.

It is a still further object of the present invention to make the surgeon's work easier and thereby reduce the psychological burden upon him in the course of a cornea operation.

The aforesaid and other objects are accomplished in an instrument for marking out the central optical zone of the cornea, comprising an oblong hollow body having the edge of one of its ends sharpened, while the diameter of the body across said end equals a preset diameter of the central optical zone, and accommodated inside the body perpendicularly to the longitudinal axis thereof is a sight formed of a pointed rod whose pointed end is arranged on the central longitudinal axis of said body.

The herein-disclosed instrument features a principle of operation based upon two factors discovered by us, namely, ability of the cornea to retain the result of plastic deformation for an adequately prolonged period of time, and the fact that the diameter of the central optical zone is in a certain relation to an expected degree of reduction of the refraction of the cornea. Hence, when in possession of a set of these instruments featuring different diameters across their sharpened edges, the surgeon may easily mark out the cornea previous to making incisions therein. Provision of a clearly outlined central optical zone precludes any possibility of penetration therein when making incisions in the cornea and hence adds to the quality and accuracy of the surgical correction of myopia. Such an instrument increases the rate of operation performance five times according to our evidence.

And last but not least, the surgeon's work is made easier and he is relieved to a great extent from mental stress, as he has the firm belief in that he will not damage the central optical zone and will obtain the desired result.

In what follows the present invention is illustrated by a detailed description of some specific embodiments thereof given with reference to the accompanying drawings, wherein.

Figure 1:
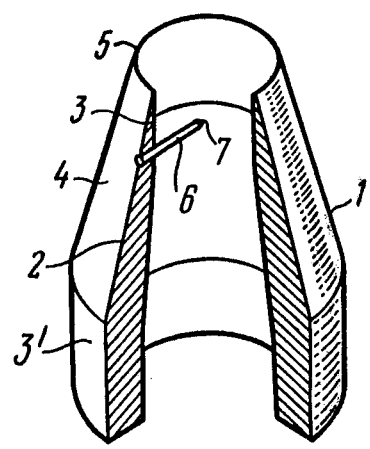
FIG. 1 is a longitudinal section view of the instrument for marking out the central optical zone of the cornea.

Reference being now directed to FIG. 1, indicated at No.1 is the instrument for marking out the central optical zone of the cornea as a whole. The instrument comprises a body 2 made of a non-toxic material, such as stainless steel, which features three portions, i.e., a portion 3 having a cylindrical inside wall a portion 4 having a conical outer wall and a portion 3' having a cylindrical outer wall. For better illumination, the inner wall of a part of the cylindrical portion 3' and part of the inner wall of the outer conical portion 4 of the instrument are conical.

Figure 2:
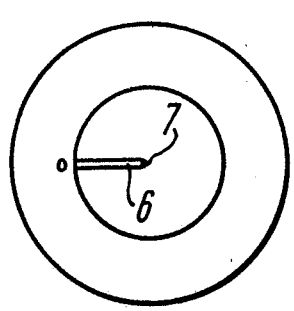
FIG. 2 is a plan view of FIG. 1.

An edge 5 of the conical portion of the instrument is sharpended to obtain a 0.1 mm thick cutting lip. A rod 6 having a pointed free end 7 is rigidly fixed, on the inner wall of the conical portion 4 of the body, where its inner surface is cylinder-shaped, the distal point of the rod's free end lying on the central axis of the body 2 (FIG. 2).

To provide better illumination special openings preferably are made in the body walls. The resulting fenestrated construction of the body is illustrated in FIG. 3.

Figure 3:
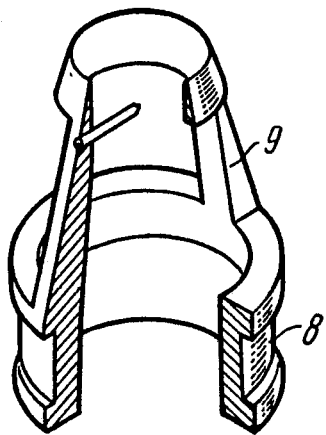
FIG. 3 is a fenestrated version of the instrument for marking out the central optical zone of the cornea.

The instrument for marking out the central optical zone of the cornea as shown in FIG. 3 is substantially similar to the instrument represented in FIG. 1, wherein the same elements in these FIGURES are identified by the same Reference Numerals, the difference between the both embodiments of the instrument residing in that the instrument of FIG. 3 has openings 9 adapted to provide better illumination of the optical zone being marked out. Besides, the instrument as is shown in FIG. 3 is provided with a circumferential groove 8 adapted to be held with the help of tweezers by the surgeon.

The instrument is grasped by the holder, using tweezers and, while bringing the central light-guiding aperture in coincidence with the optical axis of the eye, and the surgeon must force the instrument against the cornea for a 2-second period. Upon removing the instruments from the eye the cornea bears a visible impressed mark, wherefrom incisions are made towards the corneal limbus.

What we claim is:

1. An instrument for marking out the central portion of the optical zone of the cornea, comprising an oblong hollow body featuring the edge of one of its ends sharpened, while the diameter of the body across said end equals a preset diameter of the central optical zone, and a sight accommodated inside the body at right angles with the longitudinal axis thereof, a sighting point of said sight lying on the longitudinal axis of the oblong body of the instrument.

2. An instrument as claimed in claim 1, wherein the sight is made as a pointed rod, its sighting point lying on the longitudinal axis of the instrument body.

3. An instrument as claimed in claim 1, wherein the oblong body features two portions, viz., one cylindrical-shaped adapted for holding the instrument during operation, and the other conical-shaped having its edge sharpened into a cutting lip, said cylindrical and conical parts being joined together, the conical part tapering off to the cutting lip.

4. An instrument as claimed in claim 3, wherein a circumferential groove is provided on the cylindrical portion thereof for convenient holding of the instrument.

5. An instrument as claimed in claim 3, wherein openings are provided in the conical portion of the body.

6. An instrument as claimed in claim 1, wherein the body has a number of openings.

7. An instrument for marking out the central optical zone of the cornea comprising:
   a generally oblong, hollow body;
   said body having a diameter at one end thereof substantially equal to a predetermined diameter of said central optical zone;
   said end having a cutting lip; and
   sighting means secured in said body substantially perpendicularly to the longitudinal axis thereof;
   said means having a pointed inner end lying on said longitudinal axis.

8. The instrument of claim 7, wherein said body includes two portions:
   a cylindrical portion adapted for holding the instrument during operation, and a conical portion having one end sharpened into said cutting lip.

9. An instrument as claimed in claim 8, wherein gripping means are provided on said cylindrical portion for holding said instrument.

10. An instrument as claimed in claim 9, wherein openings are provided in said conical portion of the body between said gripping means and said conical portion.

11. An instrument as claimed in claim 7, including a plurality of windows to provide better illumination of the optical zone being marked out.

12. The instrument of claim 7 or 8, wherein said cutting lip is about 0.1 mm thick.

13. The instrument of claim 8, wherein said sighting means consist of a pointed rod secured to the inner wall of said conical portion, said rod having a sighting point lying on the longitudinal axis of said body.

14. The instrument of claim 8, wherein the inner wall of a part of said cylindrical portion and part of the inner wall of said conical portion are both conical.

15. A set of opthalmological instruments comprising a plurality of instruments for marking out the central optical zone of the cornea as defined in claims 7, 8 or 9 having different diameters across the cutting lip thereof for use on corneas of different diameters.

* * * * *